US009399004B2

(12) United States Patent
Qian et al.

(10) Patent No.: US 9,399,004 B2
(45) Date of Patent: Jul. 26, 2016

(54) DENTAL COMPOSITION HAVING A REDOX INDICATOR AND METHOD OF USING SAME

(75) Inventors: Xuejun Qian, Foothill Ranch, CA (US); David Tobia, Ladera Ranch, CA (US)

(73) Assignee: Kerr Corporation, Orange, CA (US)

( * ) Notice: Subject to any disclaimer, the term of this patent is extended or adjusted under 35 U.S.C. 154(b) by 948 days.

(21) Appl. No.: 13/288,420

(22) Filed: Nov. 3, 2011

(65) Prior Publication Data

US 2012/0115978 A1 May 10, 2012

Related U.S. Application Data

(60) Provisional application No. 61/410,171, filed on Nov. 4, 2010, provisional application No. 61/410,443, filed on Nov. 5, 2010, provisional application No. 61/410,565, filed on Nov. 5, 2010.

(51) Int. Cl.
*A61K 6/083* (2006.01)
*A61K 6/00* (2006.01)

(52) U.S. Cl.
CPC .............. *A61K 6/005* (2013.01); *A61K 6/0023* (2013.01); *A61K 6/0058* (2013.01); *A61K 6/083* (2013.01)

(58) Field of Classification Search
CPC ...... A61K 6/083; A61K 6/005; A61K 6/0058
USPC ....................................................... 523/116
See application file for complete search history.

(56) References Cited

U.S. PATENT DOCUMENTS

| 4,467,079 | A | * | 8/1984 | Hechenberger et al. ........ 526/90 |
| 4,567,030 | A | | 1/1986 | Yuasa et al. |
| 4,678,436 | A | | 7/1987 | Kondo et al. |
| 4,772,325 | A | | 9/1988 | Kwan et al. |
| 4,775,585 | A | | 10/1988 | Hagiwara et al. |
| 4,792,632 | A | | 12/1988 | Ellrich et al. |
| 4,911,899 | A | | 3/1990 | Hagiwara et al. |
| 5,154,762 | A | * | 10/1992 | Mitra et al. .................... 106/35 |
| 5,451,343 | A | | 9/1995 | Neckers et al. |
| 5,609,675 | A | | 3/1997 | Noritake et al. |
| 5,623,080 | A | | 4/1997 | Neckers et al. |
| 5,824,720 | A | | 10/1998 | Nowak et al. |
| 6,214,101 | B1 | | 4/2001 | Nakaseko |
| 6,703,518 | B1 | | 3/2004 | Xu et al. |
| 6,872,244 | B2 | | 3/2005 | Kobayashi et al. |
| 6,924,325 | B2 | | 8/2005 | Qian |
| 7,166,651 | B2 | | 1/2007 | Qian |
| 7,214,726 | B2 | | 5/2007 | Qian |
| 7,906,564 | B2 | | 3/2011 | Jia et al. |
| 2003/0083398 | A1 | * | 5/2003 | Kawashima et al. ......... 523/115 |
| 2005/0014861 | A1 | | 1/2005 | Qian |
| 2005/0154081 | A1 | | 7/2005 | Yin et al. |
| 2006/0004122 | A1 | | 1/2006 | Hecht et al. |
| 2007/0203257 | A1 | * | 8/2007 | Qian ............................ 523/116 |
| 2007/0264615 | A1 | * | 11/2007 | Ruppert et al. .............. 433/218 |
| 2009/0012209 | A1 | | 1/2009 | Eckhardt et al. |
| 2009/0048364 | A1 | | 2/2009 | Liu |
| 2010/0010115 | A1 | | 1/2010 | Kohro et al. |
| 2010/0240795 | A1 | | 9/2010 | Burtscher et al. |

FOREIGN PATENT DOCUMENTS

| DE | 102004031524 A1 | 1/2006 |
| DE | 102007054888 A1 | 5/2009 |
| EP | 079703 A1 | 5/1983 |
| EP | 0115410 A2 | 8/1984 |
| EP | 0541493 A1 | 5/1993 |
| EP | 1408060 A1 | 4/2004 |
| JP | 2004-051555 A | 2/2004 |
| WO | 0230363 A2 | 4/2002 |
| WO | 2007041266 A1 | 4/2007 |

OTHER PUBLICATIONS

Anonymous, Color Indicated Dental Compositions for Use as a Bonding Agent, Self-Etch Primer, and Surface Sealant, Research Disclosure, vol. 470, No. 44, Mason Publications, Hampshire, GB, Jun. 1, 2003, 2 pp.
European Patent Office, Search Report and Preliminary Opinion issued in corresponding EP Application No. 11187937.5, dated Sep. 30, 2013, 7 pp.
European Patent Office, Search Report and Preliminary Opinion issued in related EP Application No. 11187940.9, dated Oct. 2, 2013, 6 pp.
European Patent Office, Search Report and Preliminary Opinion issued in related EP Application No. 11187943.3, dated Oct. 11, 2013, 8 pp.
Database WPI Week 200418, Thomson Scientific, London, GB, XP002713349, 2 pp.

\* cited by examiner

*Primary Examiner* — Michael Pepitone
(74) *Attorney, Agent, or Firm* — Wood, Herron & Evans, LLP

(57) ABSTRACT

A self-cure or dual-cure polymerizable dental composition is provided with a redox indicator. The composition exhibits an initial first color upon mixing of the two parts and then changes to a second color that is noticeably different from the first color during the curing or polymerization of the composition initiated through the redox initiator system. Advantageously, the first color may be distinctively different from tooth structure and can be easily noticed. The second color may be essentially colorless, a neutral color, or a non-visually observable color in reference to the tooth structure.

32 Claims, No Drawings

DENTAL COMPOSITION HAVING A REDOX INDICATOR AND METHOD OF USING SAME

CROSS REFERENCE TO RELATED APPLICATION

Pursuant to 37 C.F.R. §1.78(a)(4), this application claims the benefit of and priority to prior filed Provisional Application No. 61/410,171 filed Nov. 4, 2010 and prior filed Provisional Application Nos. 61/410,443 and 61/410,565 filed Nov. 5, 2010, which are expressly incorporated herein by reference.

FIELD OF THE INVENTION

The present invention is directed to dental compositions and, more particularly, to the visual characteristics of dental restorative compositions.

BACKGROUND OF THE INVENTION

Currently, self-cure or dual-cure dental restorative materials are used as resin cements, filling materials or core buildup materials. Dentists normally wait until the material gels or sets before they remove excess material and finish (or polish) the restoration. However, the gel and set times of those materials change as the material ages due to degradation of the redox initiator, so dentists have to constantly touch the material to check if the material has gelled or set. Not only this is inconvenient, touching the material before the material gels can also affect the set quality of the material and negatively impact the mechanical property of the material. Also, if the dentist waits too long before removing the excess material, it can be quite difficult to remove the excess material as it becomes too hard to remove. Currently there is no self-cure or dual-cure restorative material that has visual characteristics that tell the dentist when the material has gelled or set so that the dentist can start removing excess material or polish the restoration.

Some dentists prefer to remove excess material immediately (i.e., before gellation) upon placement or seating of the restoration. Current self-cure or dual-cure dental restorative materials are generally tooth colored or of neutral color such that there is insufficient contrast to easily identify where the excess material is, making removing excess material difficult.

There is thus a need for a dental restorative material that has visual characteristics prior to gellation that enable easy identification and removal of excess material if a dentist prefers to remove it immediately prior to gellation. There is further a need for a dental restorative material that has visual characteristics upon gellation or hardening to enable a dentist to precisely know when to remove the excess material after gellation without the need for constantly checking to see if the material has in fact gelled.

SUMMARY OF THE INVENTION

This disclosure is directed to a polymerizable dental composition comprising (a) one or more polymerizable monomers each having at least one ethylenically unsaturated group, (b) one or more finely divided fillers having a mean particle size of less than 50 microns, (c) a reducing agent, (d) an oxidizing agent, and (e) a redox indicator. The reducing agent (c) and the oxidizing agent (d) form a redox initiator system, and upon homogenously mixing (a)-(e), the mixed composition exhibits a noticeable color change from an initial first color to a second color during the curing of the mixed composition initiated by the redox initiator system.

DETAILED DESCRIPTION OF THE INVENTION

The present invention is directed a dental restorative material that has an initial distinctive color for easy identification and removal of excess material if dentists prefer to remove it immediately prior to gellation. For dentists who prefer to remove the excess material after the material reaches its gel state, the restorative material has an initial distinctive color, and then undergoes a distinctive color transition to a different color or colorless upon gellation or hardening so that dentist can precisely know when to remove the excess material without the need for constantly checking to see if the material has gelled.

To that end, the current invention discloses a self-cure or dual-cure polymerizable dental composition containing a redox indicator. The composition exhibits an initial first color upon mixing of the two parts and then changes to a second color that is noticeably different from the first color during the curing or polymerization of the composition initiated through the redox initiator system. Advantageously, the first color may be distinctively different from tooth structure and can be easily noticed. Further advantageously, the second color is essentially colorless, a neutral color, or not easily noticeable color so that the restorative material can blend in well with the tooth structure, i.e., a non-visually observable color in reference to the tooth structure.

In one specific embodiment, a self-cure or dual-cure polymerizable dental composition comprises:

(a) one or more polymerizable monomers each having at least one ethylenically unsaturated group, (b) one or more finely divided fillers having a mean particle size of less than 50 microns, (c) a reducing agent, (d) an oxidizing agent, and (e) a redox indicator, wherein the reducing agent (c) and the oxidizing agent (d) form a redox initiator system that, when the components (a)-(e) of the composition are homogeneously mixed together, can initiate the polymerization of the polymerizable monomers (a) and cause the mixed composition to harden. The redox indicator (e) registers the reaction by initiating a color change in the composition, from an initial color that represents the uncured state, to a final color that represents completion of the redox reaction, or near completion of the redox reaction, or near the gellation point of the mixed composition. One or more shade variations between the initial color and final color may represent the degree to which the redox reaction has proceeded.

As used herein, "a" means "one or more" such that, for example, "a polymerizable monomer" means "one or more polymerizable monomers." The terms "a" and "one or more" may be used interchangeably.

This disclosure is also directed to a method of using the current inventive dental composition for identifying where the excess material is and/or when to remove the excess material.

When the composition is homogenously mixed, the reducing agent (c) and oxidizing agent (d) of the redox initiator system come into contact with each other, at which time they will undergo a redox reaction, generate free radicals, initiate the polymerization of the polymerizable monomers (a), and cause the gellation and hardening (or curing) of the composition. Immediately upon mixing, the composition would exhibit an initial first color. During the polymerization, gellation, or hardening of the composition, the redox indicator (e) will undergo a distinctive or noticeable color change to a second or final color. In one embodiment, the first color is distinctively different from tooth structure and can be easily noticed. In one embodiment, the second or final color is a colorless color, a neutral color, or an otherwise not easily noticeable color so that the dental material can blend in well with the tooth structure.

For component (a), one or more polymerizable monomers each having at least one ethylenically unsaturated group can be incorporated into the composition. Examples of ethylenically unsaturated groups include, but are not limited to, acrylate, methacrylate, acrylamide, methacrylamide, and vinyl group. Examples of polymerizable monomers include, but are not limited to, the following: hydroxyethyl(meth)acrylate {(meth)acrylate=acrylate or methacrylate}, hydroxypropyl (meth)acrylate, hydroxybutyl (meth)acrylate, glycerol di(meth)acrylate, glycerol mono(meth)acrylate, methyl (meth)acrylate, ethyl(meth)acrylate, propyl(meth)acrylate, butyl(meth)acrylate, hexyl(meth)acrylate, octyl(meth)acrylate, lauryl(meth)acrylate, decyl(meth)acrylate, tridecyl (meth)acrylate, 2-ethoxyethyl(meth)acrylate, 2'-ethoxy-2-ethoxyethyl(meth)acrylate, ethyleneglycol di(meth)acrylate, diethyleneglycol di(meth)acrylate, triethyleneglycol di(meth)acrylate (TEGDMA), tetraethyleneglycol di(meth) acrylate, polyethyleneglycol mono-(meth)acrylate, polyethyleneglycol di(meth)acrylate, polypropyleneglycol mono-(meth)acrylate, polypropyleneglycol di(meth)acrylate, polytetramethyleneglycol mono-(meth)acrylate, polytetramethyleneglycol di(meth)acrylate, hexanediol di(meth)acrylate, trimethyloylpropane tri(meth)acrylate, ethoxylated trimethyloylpropane tri(meth)acrylate, UDMA (reaction product of 2-hydroxyethyl methacrylate with 2,4,4-trimethylhexane diisocyanate), 2,2-bis[4-(2-hydroxy-3-methacryloylpropoxy)-phenyl]-propane (Bis-GMA), ethoxylated bisphenol A dimethacrylate ("EBPADMA-n", n=total number of moles of ethylene oxide in the molecule, with 2-20 units being preferred), tetrahydrofurfuryl (meth)acrylate, N,N'-methylenebis(acrylamide), N,N'-ethylenebis(acrylamide), N,N'-butylenebis(acrylamide), or a mixture thereof. In one embodiment, component (a) comprises at least one polymerizable monomer having at least one hydroxyl group. Examples of hydroxyl-containing polymerizable monomers include, but are not limited to, hydroxyethyl (meth)acrylate, hydroxypropyl (meth)acrylate, hydroxybutyl (meth)acrylate, glycerol di(meth)acrylate, glycerol mono(meth)acrylate, and 2,2-bis[4-(2-hydroxy-3-methacryloylpropoxy)-phenyl]-propane (Bis-GMA).

In one embodiment, component (a) comprises one or more polymerizable monomers having at least two ethylenically unsaturated groups.

In one embodiment, component (a) further comprises one or more acidic polymerizable monomers having at least one ethylenically unsaturated group and at least one acidic moiety. The acidic moiety can be any acidic functional group. Examples of acidic moieties include, but are not limited to, sulfonic acid, sulfinic acid, carboxylic acid, carboxylic acid anhydride, phosphonic acid or its derivative, and phosphoric acid or its derivative, with a derivative being a salt or ester of the respective acid. In one embodiment, the acidic polymerizable monomer contains at least one acidic moiety selected from the group consisting of phosphonic acid or its derivative and phosphoric acid or its derivative. Examples includes, but are not limited to, phenyl methacryloxyethyl phosphate, glyceryldimethacrylate phosphate, dipentaerithritol pentaacrylate phosphate, methacryloyloxybutyl phosphate, methacryloyloxyhexyl phosphate, methacryloyloxydecyl phosphate, hydroxyethylmethacrylate phosphate, and bis(hydroxyethylmethacrylate) phosphate, and any combination thereof. In another embodiment, the acidic monomer contains at least one acidic moiety selected from the group consisting of carboxylic acid and carboxylic anhydride. Examples includes, but are not limited to, maleic acid, itaconic acid, methacrylic acid, acrylic acid, polymerizable homopolymer or copolymer of an α,β-unsaturated carboxylic acid such as (meth)acrylated poly(acrylic acid), (meth)acrylated poly(acrylic acid) copolymer such as (meth)acrylated poly(acrylic acid-maleic acid) copolymer or (meth)acrylated poly(acrylic acid-maleic acid-itaconic acid) copolymer, maleic anhydride, 4-methacryloxyethyltrimellitic anhydride, 4-methacryloxyethyltrimellitic acid, any addition product of mono- or di-anhydride compound with an hydroxyalkylmethacrylate compound such as the addition product of pyromellitic acid anhydride and 2-hydroxyethyl methacrylate, the addition product of pyromellitic acid anhydride and glycerol dimethacrylate, the addition product of 3,3',4,4'-benzophenonetetracarboxylic dianhydride and hydroxyethyl methacrylate, the addition product of phthalic anhydride and hydroxyethyl methacrylate, the addition product of maleic anhydride and glycerol dimethacrylate, and any combination thereof.

The concentration of component (a) ranges from 1% (w/w) to 99% (w/w) of the composition. In one embodiment, the concentration of component (a) ranges from 10% (w/w) to 80% (w/w) of the composition. In one embodiment, the concentration of component (a) ranges from about 20% (w/w) to 70% (w/w) of the composition For component (b), one or more fillers can be incorporated into the composition. Examples of fillers include, but are not limited to, inorganic metal, salt, oxide, fluoride, nitride, silicate glass, aluminosilicate glass, aluminoborosilicate glass, fluoroaluminosilicate glass, quartz, colloidal silica, precipitated silica, zirconia-silica, mixed oxides fused together, polymeric filler, and/or polymerized composite fillers with inorganic particles. In one embodiment, inorganic fillers for increased x-ray contrast ability include metals, salts, oxides, fluorides, silicate glass, aluminosilicate glass, aluminoborosilicate glass, and fluoroaluminosilicate glass containing elements of high atomic number such as Sr, Y, Zr, Ba, La, Hf, Zn, Bi, W, rare earth metals, and combinations of these. Examples include barium sulfate, silver, strontium fluoride, barium fluoride, ytterbium fluoride, yttrium fluoride, barium tungstate, zinc oxide, bismuth(III) oxide, bariumaluminosilicate, bariumaluminoborosilicate, strontiumaluminosilicate, bariumfluoroaluminosilicate, strontiumfluoroaluminosilicate, strontiumzincfluoroaluminosilicate, zincaluminosilicate, etc. Fumed silica, colloidal silica, or precipitated silica can also be incorporated to improve the dispersion of the filler, as well as the rheological and handling properties of the composition. Examples of colloidal silicas are the Aerosil series such as OX-50, OX-130, and OX-200 silica sold by Degussa (Ridgefield Park, N.J.), and Cab-O-Sil M5 and Cab-O-Sil TS-530 silica sold by Cabot Corp (Tuscola, Ill.). The filler may also include nanoparticles such as those obtained through a sol-gel process. Examples include, but are not limited to those disclosed in U.S. Pat. Nos. 4,567,030 and 5,609,675, the disclosure of each expressly incorporated by reference herein in its entirety. Mixtures of different fillers can be used. For inorganic fillers, the surface of the filler may be treated or coated with a coupling agent, such as gamma-methacryloyloxypropyltrimethoxysilane (MPTMS), that enhances the interfacial bonding between the filler and resin matrix and improves mechanical properties. In one embodiment, the mean particle size of the filler is less than 50 microns. In another embodiment, the mean particle size of the filler is less than 10 microns. In another embodiment, the mean particle size of the filler is less than 5 microns. In another embodiment, the mean particle size of the filler is less than 2 microns. The concentration of component (b) ranges from 0.5% (w/w) to 90% (w/w) of the composition. In one embodiment, the concentration of component (b) is greater than 10% (w/w), for example, greater than 30% (w/w) or greater than 40% (w/w) of the composition. In one embodiment, the concentration of component (b) is less than 90% (w/w), for example, less than 80% (w/w) or less than 70% (w/w) of the composition For component (c), one or more reducing agents can be used as long as it can form a redox initiator system with component (d) that will be capable of initiating the polymerization and hardening of component (a). Examples of reducing agents include, but are not limited to, a tertiary amine, aromatic sulfinate salt, aliphatic sulfinate salt, thiourea, substituted thiourea, Fe(II) salt, Cu(I) salt, Co(II) salt, ascorbic acid, ascorbic acid derivatives and salts, barbituric acid, and barbituric acid derivatives and salts including thiobarbituric acid and it's derivatives and salts. In one embodiment, the reducing agent is an aromatic tertiary amine. Examples of aromatic tertiary amine include, but are not limited to, N,N-dihydroxyethyl p-toluidine, N,N-dimethyl p-toluidine, N,N-dimethylaminophenylethyl alcohol, and N,N-dimethylaminophenylacetic acid. In one embodiment, the reducing agent is an aromatic sulfinate salt. Examples of aromatic sulfinate salts include, but are not limited to, sodium benzenesulfinate, potassium benzenesulfinate, sodium toluenesulfinate, and potassium toluenesulfinate. In one embodiment, the reducing agent is a substituted thiourea. Substituted thioureas include, but are not limited to, 1-(2-pyridyl)-2-thiourea, 1-benzoyl-3-(2-pyridyl)-2-thiourea, 1-acetyl-3-(2-pyridyl)-2-thiourea, 1-phenyl-3-(2-pyridyl)-2-thiourea, 1-(2-pyridyl)-2-thiourea, 1,3-di-(2-pyridyl)-2-thiourea, 1,1-dimethyl-3-(2-pyridyl)-2-thiourea, 1,1,3-trimethyl-3-(2-pyridyl)-2-thiourea, and 1-(2-tetrahydrofufuryl)-3-(2-pyridyl)-2-thiourea, 1-acetyl-2-thiourea, 1-(2-tetrahydrofurfuryl)-2-thiourea, 1,1,3,3-tetramethyl-2-thiourea, 1,1,3-trimethyl-2-thiourea, 1,1,3,3-tetrapropyl-2-thiourea, 1-benzoyl-2-thiourea, and 1-benzoyl-3-methyl-2-thiourea. The concentration of component (c) ranges from 0.01% (w/w) to 10.0% (w/w) of the composition. In one embodiment, the concentration of component (c) ranges from 0.1% (w/w) to about 5.0% (w/w) of the composition.

For component (d), one or more oxidizing agents can be used as long as it can form a redox initiator system with component (c) that will be capable of initiating the polymerization and hardening of component (a). Examples of oxidizing agents include, but are not limited to, peroxide, hydroperoxide, persulfate salt, permanganate salt, Cu(II) salt such as Cu(II) acetylacetonate, Cu(II) benzoylacetonate, and Cu(II) cyclohexylbutyrate, Fe(III) salt such as $FeCl_3$, Fe(III) benzoyl acetonate, and Fe(III) cyclohexylbutyrate, and Co(III) salt. Examples of peroxides and hydroperoxides include, but are not limited to, di-t-butyl peroxide, dibenzoyl peroxide, hydrogen peroxide, t-butyl hydroperoxide, t-amyl hydroperoxide, p-diisopropylbenzene hydroperoxide, cumene hydroperoxide, pinane hydroperoxide, p-methane hydroperoxide, and 1,1,3,3-tetramethylbutyl hydroperoxide. The concentration of component (d) ranges from 0.01% (w/w) to 10.0% (w/w) of the composition. In one embodiment, the concentration of component (d) ranges from 0.1% (w/w) to about 5.0% (w/w) of the composition.

For component (e), one or more redox indicators can be used as long as the redox indicator(s) can exhibit definite (preferably noticeable) color change during the curing of the mixed composition initiated by the redox initiator system comprising component (c) and component (d). The redox indicator exhibits an initial first color upon mixing of the two parts of the redox initiator system and then changes to a second or final color that is noticeably different from the first color during the curing or polymerization of the composition through the redox initiator system. In one embodiment, the color change ($\Delta E$) during the curing of the mixed composition is at least 5. In one embodiment, the color change ($\Delta E$) during the curing of the mixed composition is at least 20. In one embodiment, the color change ($\Delta E$) during the curing of the mixed composition is at least 25. In one embodiment, the color change ($\Delta E$) during the curing of the mixed composition is at least 30. By way of example, a color change measurement may be conducted using a portable Spectrophotometer (Model SP60, X-Rite Inc.) in reflectance mode against a white background of an opacity card (Form 2A, Leneta Co.). The color is expressed as L*a*b* using the CIELAB scale where L* defines the lightness, a* denotes the red/green value, and b* the yellow/blue value. For color measurement, 1 mm thick specimens may be used. The overall color change may then be calculated using the following equation:

$$\Delta E = \{(L^*_1 - L^*_0)^2 + (a^*_1 - a^*_0)^2 + (b^*_1 - b^*_0)^2\}^{1/2}$$

where $L^*_0$, $a^*_0$, and $b^*_0$ are the initial color coordinates of initial color before color change, and $L^*_1$, $a^*_1$, and $b^*_1$ are the color coordinates after color change.

In an exemplary embodiment, the first color is quite a distinctive color that can be easily perceived so that if the dentist decides to clean the excess material immediately (i.e., before gellation), the dentist can easily identify where the excess material is. In another exemplary embodiment, the redox indicator exhibits its color change close to the gellation point of the mixed composition so that if the dentist decides to clean the excess material in its gelled state, the excess material can be easily and cleanly removed in relatively large pieces or in a single piece. In one embodiment, the redox indicator exhibits its color change within 90 seconds of the gellation point of the mixed composition. In another embodiment, the redox indicator exhibits its color change within 60 seconds of the gellation point of the mixed composition. In yet another embodiment, the redox indicator exhibits its color change within 30 seconds of the gellation point of the mixed composition. In yet another embodiment, the redox indicator exhibits its color change within 15 seconds of the gellation point of the mixed composition. In yet another embodiment, the redox indicator exhibits its color change within 5 seconds of the gellation point of the mixed composition. The gellation point is a point at which an infinite polymer network first appears. In an exemplary embodiment, the second color is a colorless color, a neutral color or a not easily noticeable color so that the dental material does not leave an undesirable color after the material is fully set, resulting in improved esthetics for the restoration or other dental structure.

Examples of redox indicators include, but are not limited to, 2,2'-bipyridine (Ru complex), nitrophenanthroline (Fe complex), 1,10-phenanthroline (Fe complex), N-phenylanthranilic acid, N-ethoxychrysoidine, 2,2'-bipyridine (Fe complex), 5,6-dimethylphenanthroline (Fe complex), o-dianisidine, sodium diphenylamine sulfonate, diphenylbenzidine, diphenylamine, viologen, sodium 2,6-dibromophenol-indophenol, sodium 2,6-dichlorophenol-indophenol, sodium o-cresol indophenol, thionine acetate, 3,7-bis(dimethylamino)-phenothiazin-5-ium chloride, indigotetrasulfonic acid, indigotrisulfonic acid, 5,5'-indigodisulfonic acid sodium salt, indigomono sulfonic acid, phenosafranin, safranin T, and toluylene red. In one embodiment, the redox indicators are selected from the group consisting of N-phenylanthranilic acid, o-dianisidine, sodium diphenylamine sulfonate, diphenylbenzidine, diphenylamine, sodium 2,6-dibromophenol-indophenol, sodium 2,6-dichlorophenol-indophenol, sodium o-cresol indophenol, thionine acetate, 3,7-bis(dimethylamino)-phenothiazin-5-ium chloride, indigotetrasulfonic acid, indigotrisulfonic acid, 5,5'-indigodisulfonic acid sodium salt, indigomono sulfonic acid, phenosafranin, safranin T, and toluylene red. In another embodiment, the redox indicators are selected from the group consisting of sodium 2,6-dibromophenol-indophenol, sodium 2,6-dichlorophenol-indophenol, sodium o-cresol indophenol, thionine acetate, 3,7-bis(dimethylamino)-phenothiazin-5-ium chloride, indigotetrasulfonic acid, indigotrisulfonic acid, 5,5'-indigodisulfonic acid sodium salt, indigomono sulfonic acid, phenosafranin, safranin T, and toluylene red. In yet another embodiment, the redox indicators are selected from the group consisting of Sodium 2,6-dibromophenol-indophenol, sodium 2,6-dichlorophenol-indophenol, and sodium o-cresol indophenol.

In one embodiment, at least one of the reducing agent (c), oxidizing agent (d), and redox indicator (e) is microencapsulated. Microencapsulation may be achieved by methods known to one skilled in the art, for example using water soluble or water insoluble encapsulants.

The composition can further comprise one or more components selected from the group consisting of a photo-initiator system, an acidic polymer, a solvent, a colorant, a stabilizer, a UV stabilizer, a fluoride compound, and an antimicrobial agent.

In one embodiment, the composition further comprises a photoinitiator. The photoinitiator can be any compound that would generate free radicals upon exposure to a light source and cause the polymerization or hardening of the composition. The light source can be any dental curing light that emits light in the visible or ultraviolet range. Examples of photoinitiators include, but are not limited to, benzoin, benzoin ethers and esters, 2,2-diethoxy acetophenone, diketone compounds such as camphorquinone and 1-phenyl-1,2-propanedione, monoacylphosphine oxide, bisacylphosphine oxide as disclosed in U.S. Pat. No. 4,792,632, which is expressly incorporated by reference herein in its entirety, diaryliodonium salt, triarylsulfonium salt, and a mixture of photoinitiators.

Additionally, a coinitiator can be used together with a photoinitiator to enhance curing efficiency. Coinitiators include tertiary amine and sulfinate compounds. Examples of coinitiators include, but are not limited to, ethyl 4-(N,N-dimethylamino)benzoate, 4-(N,N-dimethylamino)benzoic acid, 4-(N,N-dimethylamino)benzonitrile, 4-(N,N-dimethylamino)benzaldehyde, 2-(ethylhexyl)-4-(N,N-dimethylamino)benzoate, N,N-dimethylaminoethyl methacrylate, N,N-dimethylaminophenethyl alcohol, sodium benzenesulfinate, and sodium toluenesulfinate.

In one embodiment, a photoinitiator system includes the combination of camphorquinone and a tertiary amine. Examples of tertiary amines include, but are not limited to, ethyl 4-(N,N-dimethylamino) benzoate, 4-(N,N-dimethylamino) benzoic acid, 4-(N,N-dimethylamino)benzonitrile, 4-(N,N-dimethylamino) benzaldehyde, 2-(ethylhexyl)-4-(N,N-dimethylamino)benzoate, N,N-dimethylaminoethyl methacrylate, N,N-dimethylaminophenethyl alcohol. In another embodiment, a photoinitiator system includes bisacylphosphine oxide or monoacylphosphine oxide or the combination of camphorquinone and bisacylphosphine oxide or monoacylphosphine oxide. In one embodiment, a photoinitiator may be present at a concentration of 0.01% (w/w) to about 10% (w/w) of the composition. In another embodiment, a photoinitiator may be present at a concentration of 0.05% (w/w) to about 5% (w/w) of the composition.

In one embodiment, the composition further comprises an acidic polymer. Examples of acidic polymers include, but are not limited to, a homopolymer or copolymer of an α,β-unsaturated carboxylic acid. Examples of homopolymer or copolymer of an α,β-unsaturated carboxylic acid include, but are not limited to, poly(acrylic acid), poly(acrylic acid-maleic acid) copolymer, and poly(acrylic acid-maleic acid-itaconic acid) copolymer.

In one embodiment, the composition further comprises a solvent. Useful solvents include water, methanol, ethanol, isopropanol, acetone, methyl ethyl ketone, ethylene glycol, and glycerin. In one embodiment, the solvent is water.

Other ingredients can also be incorporated into the composition of the current invention, such as a colorant, a stabilizer, a UV stabilizer, a fluoride compound, and/or an antimicrobial agent. The colorants are used to achieve desired shade for matching tooth color and can be inorganic pigments or organic dyes. The stabilizer is a polymerization inhibitor or retarder to improve the shelf stability of the restorative material. Most commonly used stabilizers include 2,6-di-(tert-butyl)-4-methylphenol ("BHT") and 4-methoxyphenol ("MEHQ"). The UV absorber is used to improve the color stability of the dental material upon exposure to UV light. An example of UV absorber is 2-hydroxy-4-methoxybenzophenone ("UV-9"). A fluoride compound is any fluoride-containing substance that can release fluoride into saliva or water. Examples of fluoride compounds include, but are not limited to, sodium fluoride, strontium fluoride, sodium hexafluorosilicate, zinc hexafluorosilicate, ytterbium fluoride, a salt formed by an amine and HF, a complex formed by an amine and $BF_3$, and any combination thereof. Examples of antimicrobial additives include, but are not limited to, benzalkonium chloride, iodoform, eugenol, zinc oxide, triclosan, alkyl 4-hydroxybenzoate, silicate glass powder containing silver and/or zinc, and zeolite powder containing silver and/or zinc ion(s). Useful antibacterial zeolites and their preparation are disclosed in U.S. Pat. Nos. 4,911,899 and 4,775,585, each of which is expressly incorporated by reference herein in its entirety.

In one embodiment, the composition is a two-part composition. Any part of the two-part composition can be in any form selected from the group consisting of a powder, a liquid, and a paste. In one embodiment, the two-part composition is a liquid/powder composition (i.e., one part is in a liquid form and the other part is in a powder form). In one embodiment, the two-part composition is a paste/paste composition (i.e., one part is in a paste form and the other part is also in a paste form). In one embodiment, the two-part composition is a liquid/paste composition (i.e. one part is in a liquid form and the other part is in a paste form). Any mixing ratio of the two parts can be used. In one embodiment, the mixing ratio of the two parts is between 0.02:1 to 50:1 (weight ratio). In another embodiment, the mixing ratio of the two parts is between 0.05:1 to 20:1 (weight ratio). In another embodiment, the mixing ratio of the two parts is between 0.1:1 to 10:1 (weight ratio). In another embodiment, the mixing ratio of the two parts is between 0.2:1 to 5:1 (weight ratio).

In various embodiments, the reducing agent (c) and oxidizing agent (d) are incorporated into separate parts, or one or both of them is microencapsulated and they are both in the same part or in separate parts.

In one embodiment, the dental composition is a self-cure dental composition (i.e., curing without the activation of light). In another embodiment, the dental composition is a dual-cure dental composition (both self-cure and photo-cure)

when a photo-initiator is also included. When the composition is homogeneously mixed and self-cured (without photo-curing), the mixed composition will set (or harden) within about 20 minutes. In embodiments, setting occurs within about 10 minutes from the start of mixing, or within about 5 minutes from the start of mixing.

Mixing of the two parts can be achieved by any mixing means. For example, the parts may be mixed manually using a spatula, or a mixing stick, etc. They may be mixed using an automated mixer, such as an amalgamator or a Rotomix™ (3M ESPE, St. Paul, Minn.). The use of an automatic or static mixer can result in a significant time saving for the dental practitioner. Mechanical properties of the mixed composition are also enhanced when using an automated mixer or static mixer because air bubbles are minimized, compared to hand mixing.

The two parts may be pre-packaged in a single dose form. In this form, the parts are packaged separately and, in use, the contents are mixed. For example, the two parts are packaged within a single capsule without contacting each other. The capsule is then placed on the amalgamator or Rotomix™ and the composition is automatically mixed. The packaging material, along with any remaining composition is discarded after each application. Such a single use packaging device eliminates a dental practitioner's concern of cross-contamination and adds convenience to inventory, storage, etc.

In one embodiment, the composition is a two-part paste/paste composition and the two pastes are packaged in two separate syringes. In another embodiment, the composition is a two-part paste/paste composition and the two pastes are packaged in a dual-barrel cartridge assembly. Each barrel in the cartridge assembly contains an exit opening. The pastes are dispensed by applying pressure to the plunger for each barrel. A static mixer may be attached to the two exit openings of the two barrels and the two pastes are mixed in a static mixer to achieve a substantially homogenous composition, and the mixed composition flows out from the exit opening.

In one embodiment, a two-part paste/paste self-cure or dual-cure dental composition containing a redox indicator consists of a first paste comprising a polymerizable monomer, a reducing agent, one or more finely divided fillers, and a redox indicator; and a second paste comprising a polymerizable monomer, an oxidizing agent, and one or more finely divided fillers. In one embodiment, the above paste/paste composition can further comprise a photo-initiator which can be incorporated into either one or both pastes. In an exemplary embodiment, the photo-initiator is incorporated into the first paste containing the reducing agent. In another embodiment, the above paste/paste composition can further comprise an acidic polymerizable monomer having at least one ethylenically unsaturated group and at least one acidic moiety, as described above in reference to component (a).

The composition of the current invention provides a dentist with a visual (color) indicator as to where the excess material is and/or when the material has gelled or set so that excess material can be removed or the restoration can be polished. This will offer dentists significant convenience and peace of mind when using this unique dental material. There is no need of constantly checking the material if it has gelled or set. If the dentist prefers to remove the excess material before it reaches its gel state, the dentist can easily identify where the excess material is.

The invention also includes methods of using the above self-cure or dual-cure dental composition comprising a redox indicator. In one embodiment, the method includes the steps: 1) homogeneously mixing the components of the dental composition just prior to application; 2) applying the mixed composition to tooth structure and/or a prosthetic device with the mixed composition exhibiting a first color that is noticeably different from the tooth structure and the prosthetic device; 3) removing any excess dental composition from the tooth structure and/or prosthetic device before the dental composition changes its color as it can be easily differentiated from the tooth structure and the prosthetic device; and 4) finishing/polishing the restoration or other dental structure after the dental composition changes to its second color that is noticeably different from its first color (i.e., after the gellation and/or the hardening of the composition). The method additionally includes a step of covering the dental composition with an oxygen barrier after step 3) to provide a more thorough curing of the dental composition without an oxygen-inhibited layer on the surface. The oxygen barrier can be a try-in gel or a glycerine gel that can be easily removed after the curing of the dental composition. The method additionally includes a step of light-curing the dental composition prior to step 4) when a photo-initiator is incorporated into the dental composition. The prosthetic device includes an inlay, an onlay, a crown, a crown and bridge, and a post.

In another embodiment, the method includes the steps: 1) homogeneously mixing the components of the dental composition just prior to application; 2) applying the mixed composition to tooth structure and/or a prosthetic device with the mixed composition exhibiting a first color; 3) removing any excess dental composition from the tooth structure and/or prosthetic device when the dental composition changes its color to a second color that is noticeably different from the first color (indicating the gellation and/or hardening of the dental composition); and 4) finishing/polishing the restoration or other dental structure. The method additionally includes a step of light-curing the restorative composition prior to step 4) when a photo-initiator is incorporated into the dental composition.

The self-cure or dual-cure dental composition comprising a redox indicator can be used as a dental restorative composition, an endodontic composition, and an orthodontic composition. The self-cure or dual-cure dental composition comprising a redox indicator can be used as a cement for adhering a prosthetic device to tooth structure, a filling material, a core buildup material, liner/base, a pit/fissure sealant, an endodontic sealing and/or filling material for sealing and/or filling of a root canal, or an orthodontic adhesive and/or cement material for adhering an orthodontic appliance to tooth surfaces. The prosthetic device includes an inlay, an onlay, a crown, a crown and bridge, and a post. In one embodiment, the self-cure or dual-cure dental composition comprising a redox indicator is used as a cement or a core buildup material.

EXAMPLES

Abbreviations for materials used in all examples:
BHT: 2,6-di-(tert-butyl)-4-methylphenol
Bis-GMA: 2,2-bis[4-(2-hydroxy-3-methacryloylpropoxy)-phenyl]-propane
CHPO: cumene hydroperoxide
CQ: camphoroquinone
EBPADMA: ethoxylated bisphenol A dimethacrylate with 3-4 moles of ethylene oxide
EDMAB: ethyl 4-(N,N-dimethylamino) benzoate
GDM-P: glyceryldimethacrylate phosphate or glyceryldimethacrylate dihydrogen phosphate
NaDCPIP: sodium 2,6-dichlorophenol-indophenol
ODMAB: 2-ethylhexyl 4-(N,N-dimethylamino) benzoate
PTU: 1-(2-pyridyl)-2-thiourea ST-BAS: bariumaluminoborosilicate filler, mean particle size of 1.6 µm, and surface treated with γ-methacryloyloxypropyltrimethoxysilane TEGDMA: triethylenglycol dimethacrylate TS-530: surface treated fumed silica or colloidal silica (from Cabot Corp.)

UDMA: reaction product of 2-hydroxyethyl methacrylate with 2,4,4-trimethylhexane diisocyanate $YbF_3$: ytterbium fluoride (aggregated 40 nm ytterbium fluoride, and mean particle size of aggregated particle of 0.7 µm)

All two-part self-curable or dual-curable (i.e. self-curable and light-curable) compositions were formulated by first mixing together all the monomers and any ingredients soluble in the resin mixture to make a homogeneous liquid mixture, and then blending the fillers into the liquid mixture to make the paste.

Comparative Example 1

A base paste composition and a catalyst paste composition were made without any redox indicator. The base paste was made by mixing the following ingredients into a homogeneous composition: 3.45% w/w Bis-GMA; 8.31% w/w TEGDMA; 11.46% w/w EBPADMA; 10.87% w/w UDMA; 0.41% w/w PTU; 3.00% w/w TS-530; 47.50% w/w ST-BAS; and 15.00% w/w $YbF_3$. The catalyst paste was made by mixing the following ingredients into a homogeneous composition: 3.45% w/w Bis-GMA; 8.21% w/w TEGDMA; 10.97% w/w EBPADMA; 10.65% w/w UDMA; 0.05% w/w BHT; 1.17% w/w CHPO; 3.00% w/w TS-530; 47.50% w/w ST-BAS; and 15.00% w/w $YbF_3$. When the base paste and catalyst paste were mixed at 1:1 volume ratio, the mixed material gelled after 4 minutes 15 seconds and hardened (or set) after 5 minutes 15 seconds. The total color change ($\Delta E$) from 2 minutes after mixing to 6 minutes after mixing was 4.9. The color change prior to and after gellation was quite small and not easily noticeable. The color of the material prior to gellation and after gellation was almost colorless.

Example 1

A base paste composition was made by introducing 0.01% w/w NaDCPIP (redox indicator) into the base paste of Comparative Example 1, and the base paste was then mixed with the catalyst paste of Comparative Example 1 at a 1:1 volume ratio. The mixed material gelled after 5 minutes and hardened (or set) after 5 minutes 45 seconds. The total color change ($\Delta E$) from 2 minutes after mixing to 6 minutes after mixing was 41.3. The color change prior to and after gellation was quite significant and easily noticeable. The color of the material changed from dark purple prior to gellation to colorless after gellation.

Example 2

A catalyst paste composition was made by introducing 0.01% w/w NaDCPIP (redox indicator) into the catalyst paste of Comparative Example 1, and the catalyst paste was then mixed with the base paste of Comparative Example 1 at a 1:1 volume ratio. The mixed material gelled after 5 minutes and hardened (or set) after 6 minutes. The total color change ($\Delta E$) from 2 minutes after mixing to 6 minutes after mixing was 25.2. The color of the material changed from light purple color prior to gellation to colorless after gellation. The color change prior to and after gellation for the mixture was much less than that observed when the redox indicator is incorporated in the base paste as in Example 1. The initial purple color is not as intense as that in Example 1 and this could be due to possible stability issues when the redox indicator is incorporated in the catalyst paste.

Comparative Example 2

A base paste composition and a catalyst paste composition were made without any redox indicator. An acidic monomer GDM-P was incorporated into the catalyst paste. The base paste was made by mixing the following ingredients into a homogeneous composition: 3.45% w/w Bis-GMA; 8.63% w/w TEGDMA; 11.39% w/w EBPADMA; 10.51% w/w UDMA; 0.53% w/w PTU; 3.00% w/w TS-530; 47.50% w/w ST-BAS; and 15.00% w/w $YbF_3$. The catalyst paste was made by mixing the following ingredients into a homogeneous composition: 3.45% w/w Bis-GMA; 7.58% w/w TEGDMA; 10.34% w/w EBPADMA; 9.65% w/w UDMA; 1.72% w/w GDM-P; 0.05% w/w BHT; 1.72% w/w CHPO; 3.00% w/w TS-530; 47.50% w/w ST-BAS; and 15.00% w/w $YbF_3$. When the base paste and catalyst paste were mixed at a 1:1 volume ratio, the mixed material gelled after 2 minutes and hardened (or set) after 3 minutes. The total color change ($\Delta E$) from 1 minute after mixing to 4 minutes after mixing was 5.0. The color change prior to and after gellation was quite small and not easily noticeable. The color of the material prior to gellation and after gellation was almost colorless.

Example 3

A base paste composition was made by introducing 0.01% w/w NaDCPIP (redox indicator) into the base paste of Comparative Example 2, and the base paste was then mixed with the catalyst paste of Comparative Example 2 at 1:1 volume ratio. The mixed material gelled after 2 minutes 30 seconds and hardened (or set) after 3 minutes 30 seconds. The total color change ($\Delta E$) from 1 minute after mixing to 4 minutes after mixing was 44.6. The color change prior to and after gellation was quite significant and easily noticeable. The color of the material changed from dark purple prior to gellation to colorless after gelation.

Example 4

A catalyst paste composition was made by introducing 0.01% w/w NaDCPIP (redox indicator) into the catalyst paste of Comparative Example 2, and the catalyst paste was then mixed with the base paste of Comparative Example 2 at a 1:1 volume ratio. The mixed material gelled after 2 minutes 45 seconds and hardened (or set) after 3 minutes 45 seconds. The total color change ($\Delta E$) from 1 minute after mixing to 6 minutes after mixing was 38.6. The color change prior to and after gellation was quite significant and easily noticeable. The color of the material changed from purple color prior to gellation to colorless after gellation. The presence of the acidic monomer in the catalyst paste improved the color change by the redox indicator, as compared to Example 2.

Comparative Example 3

A base paste composition and a catalyst paste composition were made without any redox indicator. A photoinitiator system consisting of CQ and EDMAB was incorporated into the base paste. The base paste was made by mixing the following ingredients into a homogeneous composition: 3.45% w/w Bis-GMA; 8.28% w/w TEGDMA; 11.38% w/w EBPADMA; 10.69% w/w UDMA; 0.41% w/w PTU; 0.07% w/w CQ;

0.22% w/w EDMAB; 3.00% w/w TS-530; 47.50% w/w ST-BAS; and 15.00% w/w YbF$_3$. The catalyst paste was made by mixing the following ingredients into a homogeneous composition: 3.45% w/w Bis-GMA; 8.21% w/w TEGDMA; 10.97% w/w EBPADMA; 10.65% w/w UDMA; 0.05% w/w BHT; 1.17% w/w CHPO; 3.00% w/w TS-530; 47.50% w/w ST-BAS; and 15.00% w/w YbF$_3$. When the base paste and catalyst paste were mixed at 1:1 volume ratio, the mixed material gelled after 3 minutes 45 seconds and hardened (or set) after 4 minutes 45 seconds. The total color change (ΔE) from 1 minute after mixing to 5 minutes after mixing was 6.4. The color change prior to and after gellation was quite small and not easily noticeable. The color of the material prior to gellation and after gellation was almost colorless.

Example 5

A base paste composition was made by introducing 0.01% w/w NaDCPIP (redox indicator) into the base paste of Comparative Example 3, and the base paste was then mixed with the catalyst paste of Comparative Example 3 at a 1:1 volume ratio. The mixed material gelled after 4 minutes 45 seconds and hardened (or set) after 5 minutes 45 seconds. The total color change (ΔE) from 1 minute after mixing to 5 minutes after mixing was 46.4. The color change prior to and after gellation was quite significant and easily noticeable. The color of the material changed from dark purple prior to gellation to almost colorless after gellation.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. A method of using a color-changing polymerizable dental composition, in which the composition comprises:
    (a) one or more polymerizable monomers each having at least one ethylenically unsaturated group,
    (b) one or more finely divided fillers having a mean particle size of less than 50 microns,
    (c) a reducing agent,
    (d) an oxidizing agent, and
    (e) a redox indicator,
    wherein the composition is a two-part system with the first part comprising at least one of the one or more polymerizable monomers (a), the reducing agent (c), and at least one of the one or more finely divided fillers (b); and the second part comprising at least one of the one or more polymerizable monomers (a), the oxidizing agent (d), and at least one of the one or more finely divided fillers (b), and the redox indicator (e) is incorporated into either of the first or second parts, and wherein the reducing agent (c) and the oxidizing agent (d) form a redox initiator system,
    the method comprising the steps of:
        1) homogeneously mixing the first and second parts just prior to application to form a mixed composition, wherein the mixing initiates polymerization by the redox initiator system;
        2) applying the mixed composition to a tooth structure and/or a prosthetic device with the mixed composition exhibiting a first color that is noticeably different from the tooth structure and/or prosthetic device, wherein the mixed composition exhibits a color change from the first color to a second color that is noticeably different from the first color during the polymerization;
        3) removing any excess of the mixed composition from the tooth structure and/or prosthetic device before the mixed composition changes to the second color to form a structure; and
        4) finishing/polishing the structure after the mixed composition changes to the second color, wherein the prosthetic device is selected from the group consisting of an inlay, an onlay, a crown, a crown and bridge, and a post.

2. The method of claim 1 further comprising covering the mixed composition with an oxygen barrier after step 3) to provide a more thorough curing of the mixed composition without an oxygen-inhibited layer on the surface.

3. The method of claim 1, wherein the one or more polymerizable monomers (a) includes:
    (a)(i) one or more polymerizable monomers each having at least one ethylenically unsaturated group, and
    (a)(ii) one or more acidic polymerizable monomers having at least one ethylenically unsaturated group and at least one acidic moiety, wherein the acidic moiety is selected from the group consisting of phosphonic acid or its derivative, phosphoric acid or its derivative, and any combination thereof,
    wherein the filler (b) is selected from the group consisting of metals, salts, oxides, fluorides, silicate glass, aluminosilicate glass, aluminoborosilicate glass, and fluoroaluminosilicate glass containing elements of high atomic number selected from Sr, Y, Zr, Ba, La, Hf, Zn, Bi, W, rare earth metals, and combinations thereof, and
    wherein the reducing agent (c) is a substituted thiourea reducing agent.

4. The method of claim 3 wherein the one or more acidic polymerizable monomers (a)(ii) and the redox indicator (e) are incorporated in the second part.

5. The method of claim 1 wherein the composition further comprises a photoinitiator system, the method further comprising subjecting the mixed composition to a light source to further cure the mixed composition after (3) and prior to (4).

6. The method of claim 1 wherein the concentration of the one or more finely divided fillers ranges from 0.5% (w/w) to 90% (w/w) of the mixed composition.

7. The method of claim 1 wherein the oxidizing agent is selected from the group consisting of a peroxide, a hydroperoxide, a persulfate salt, a permanganate salt, a Cu(II) salt, a Fe(III) salt, a Co(III) salt, and any combination thereof.

8. The method of claim 1 wherein the color change (ΔE) of the mixed composition is at least 20.

9. The method of claim 1 wherein the second color is a colorless color, or a color that is close to that of the tooth structure to which the mixed composition is applied.

10. The method of claim 1 wherein redox indicator is selected from the group consisting of 2,2'-bipyridine (Ru complex), nitrophenanthroline (Fe complex), 1,10-phenanthroline (Fe complex), N-phenylanthranilic acid, N-ethoxychrysoidine, 2,2'-bipyridine (Fe complex), 5,6-dimethylphenanthroline (Fe complex), o-dianisidine, sodium diphenylamine sulfonate, diphenylbenzidine, diphenylamine, viologen, sodium 2,6-dibromophenol-indophenol, sodium 2,6-dichlorophenol-indophenol, sodium o-cresol indophenol, thionine acetate, 3,7-bis(dimethylamino)-phenothiazin-5-ium chloride, indigotetrasulfonic acid, indigotrisulfonic acid, 5,5'-indigodisulfonic acid sodium salt, indigomono sulfonic acid, phenosafranin, safranin T, toluylene red, and a combination thereof.

11. The method of claim 1 wherein each of the first and second parts is packaged in a separate syringe prior to (1).

12. The method of claim 1 wherein each of the first and second parts is packaged in a syringe of a dual-syringe assembly prior to (1) wherein each syringe in the dual-syringe assembly has an opening and a static mixer is attached to the openings and (1) is performed by dispensing the first and second parts from the syringes through the openings and into the mixer and homogeneously mixing in the mixer to form the mixed composition, and (2) is performed in part by dispensing the mixed composition from an exit opening of the mixer.

13. The method of claim 1 wherein the redox indicator is incorporated in the first part.

14. A method of using a color-changing polymerizable dental composition, in which the composition comprises:
  (a) one or more polymerizable monomers each having at least one ethylenically unsaturated group,
  (b) one or more finely divided fillers having a mean particle size of less than 50 microns,
  (c) a reducing agent,
  (d) an oxidizing agent, and
  (e) a redox indicator,
  wherein the composition is a two-part system with the first part comprising at least one of the one or more polymerizable monomers (a), the reducing agent (c), and at least one of the one or more finely divided fillers (b); and the second part comprising at least one of the one or more polymerizable monomers (a), the oxidizing agent (d), and at least one of the one or more finely divided fillers (b), and the redox indicator (e) is incorporated into either of the first or second parts, and wherein the reducing agent (c) and the oxidizing agent (d) form a redox initiator system,
  the method comprising the steps of:
    1) homogeneously mixing the first and second parts just prior to application to form a mixed composition, wherein the mixing initiates polymerization by the redox initiator system;
    2) applying the mixed composition to a tooth structure and/or a prosthetic device with the mixed composition exhibiting a first color, wherein the mixed composition exhibits a color change from the first color to a second color that is noticeably different from the first color during the polymerization;
    3) removing any excess composition from the tooth structure and/or prosthetic device when the mixed composition changes color to the second color that is noticeably different from the first color and that indicates a gellation and/or hardening of the mixed composition to form a structure; and
    4) finishing/polishing the structure, wherein the prosthetic device is selected from the group consisting of an inlay, an onlay, a crown, a crown and bridge, and a post.

15. The method of claim 14, wherein the one or more polymerizable monomers (a) includes:
  (a)(i) one or more polymerizable monomers each having at least one ethylenically unsaturated group, and
  (a)(ii) one or more acidic polymerizable monomers having at least one ethylenically unsaturated group and at least one acidic moiety, wherein the acidic moiety is selected from the group consisting of phosphonic acid or its derivative, phosphoric acid or its derivative, and any combination thereof,
  wherein the filler (b) is selected from the group consisting of metals, salts, oxides, fluorides, silicate glass, aluminosilicate glass, aluminoborosilicate glass, and fluoroaluminosilicate glass containing elements of high atomic number selected from Sr, Y, Zr, Ba, La, Hf, Zn, Bi, W, rare earth metals, and combinations thereof, and wherein the reducing agent (c) is a substituted thiourea reducing agent.

16. The method of claim 14 wherein the composition further comprises a photoinitiator system, the method further comprising subjecting the mixed composition to a light source to further cure the mixed composition after (3) and prior to (4).

17. The method of claim 14 wherein the concentration of the one or more finely divided fillers ranges from 0.5% (w/w) to 90% (w/w) of the mixed composition.

18. The method of claim 14 wherein the oxidizing agent is selected from the group consisting of a peroxide, a hydroperoxide, a persulfate salt, a permanganate salt, a Cu(II) salt, a Fe(III) salt, a Co(III) salt, and any combination thereof.

19. The method of claim 14 wherein the color change ($\Delta E$) of the mixed composition is at least 20.

20. The method of claim 14 wherein the second color is a colorless color, or a color that is close to that of the tooth structure to which the mixed composition is applied.

21. The method of claim 14 wherein redox indicator is selected from the group consisting of 2,2'-bipyridine (Ru complex), nitrophenanthroline (Fe complex), 1,10-phenanthroline (Fe complex), N-phenylanthranilic acid, N-ethoxychrysoidine, 2,2'-bipyridine (Fe complex), 5,6-dimethylphenanthroline (Fe complex), o-dianisidine, sodium diphenylamine sulfonate, diphenylbenzidine, diphenylamine, viologen, sodium 2,6-dibromophenol-indophenol, sodium 2,6-dichlorophenol-indophenol, sodium o-cresol indophenol, thionine acetate, 3,7-bis(dimethylamino)-phenothiazin-5-ium chloride, indigotetrasulfonic acid, indigotrisulfonic acid, 5,5'-indigodisulfonic acid sodium salt, indigomono sulfonic acid, phenosafranin, safranin T, toluylene red, and a combination thereof.

22. The method of claim 14 wherein each of the first and second parts is packaged in a separate syringe prior to (1).

23. The method of claim 14 wherein each of the first and second parts is packaged in a syringe of a dual-syringe assembly prior to (1) wherein each syringe in the dual-syringe assembly has an opening and a static mixer is attached to the openings and (1) is performed by dispensing the first and second parts from the syringes through the openings and into the mixer and homogeneously mixing in the mixer to form the mixed composition, and (2) is performed in part by dispensing the mixed composition from an exit opening of the mixer.

24. The method of claim 14 wherein the redox indicator is incorporated in the first part.

25. The method of claim 15, wherein the substituted thiourea is 1-(2-pyridyl)-2-thiourea.

26. The method of claim 15, wherein the one or more acidic polymerizable monomers is selected from the group consisting of phenyl methacryloxyethyl phosphate, glyceryldimethacrylate phosphate, dipentaerithritol pentaacrylate phosphate, methacryloyloxybutyl phosphate, methacryloyloxyhexyl phosphate, methacryloyloxydecyl phosphate, hydroxyethylmethacrylate phosphate, and bis(hydroxyethylmethacrylate) phosphate, and combinations thereof.

27. The method of claim 15 wherein the one or more acidic polymerizable monomers (a)(ii) and the redox indicator (e) are incorporated in the second part.

28. A method of using a color-changing polymerizable dental composition, in which the composition is a two-paste system with the first paste comprising at least one of two or more polymerizable monomers (a), at least one finely divided filler (b), a reducing agent (c), a redox indicator (e), and a photoinitiator (f), and the second paste comprising at least one of the two or more polymerizable monomers (a), at least one finely divided filler (b) that is the same or different than the filler (b) in the first paste, and an oxidizing agent (d), wherein the at least two polymerizable monomers (a) include (i) one or more polymerizable monomers each having at least one ethylenically unsaturated group, and (ii) one or more acidic polymerizable monomers having at least one ethylenically unsaturated group and at least one acidic moiety, wherein the acidic moiety is selected from the group consisting of phosphonic acid or its derivative, phosphoric acid or its derivative, and any combination thereof, the method comprising the steps of:

1) homogeneously mixing the first and second pastes just prior to application to form a mixed composition exhibiting a first color and in which the reducing agent (c) and the oxidizing agent (d) form a redox initiator system that reacts to initiate polymerization of the at least two polymerizable monomers (a);
2) applying the mixed composition of the first color to a tooth structure and/or a prosthetic device;
3) removing any excess composition from the tooth structure and/or prosthetic device when the mixed composition changes color to a second color that is noticeably different from the first color and that indicates a gellation and/or hardening of the mixed composition to form a structure;
4) exposing the structure to a light source to generate free radicals from the photoinitiator in the mixed composition to cause further polymerization of the at least two polymerizable monomers (a); and
5) finishing/polishing the structure, wherein the prosthetic device is selected from the group consisting of an inlay, an onlay, a crown, a crown and bridge, and a post.

29. The method of claim 28 wherein the filler (b) in each of the first and second pastes is selected from the group consisting of metals, salts, oxides, fluorides, silicate glass, aluminosilicate glass, aluminoborosilicate glass, and fluoroaluminosilicate glass containing elements of high atomic number selected from Sr, Y, Zr, Ba, La, Hf, Zn, Bi, W, rare earth metals, and combinations thereof, and wherein the oxidizing agent is selected from the group consisting of a peroxide, a hydroperoxide, a persulfate salt, a permanganate salt, a Cu(II) salt, a Fe(III) salt, a Co(III) salt, and any combination thereof.

30. The method of claim 28 wherein the color change ($\Delta E$) of the mixed composition is at least 20, wherein the second color is a colorless color, or a color that is close to that of the tooth structure to which the mixed composition is applied, and wherein redox indicator is selected from the group consisting of 2,2'-bipyridine (Ru complex), nitrophenanthroline (Fe complex), 1,10-phenanthroline (Fe complex), N-phenylanthranilic acid, N-ethoxychrysoidine, 2,2'-bipyridine (Fe complex), 5,6-dimethylphenanthroline (Fe complex), o-dianisidine, sodium diphenylamine sulfonate, diphenylbenzidine, diphenylamine, viologen, sodium 2,6-dibromophenol-indophenol, sodium 2,6-dichlorophenol-indophenol, sodium o-cresol indophenol, thionine acetate, 3,7-bis(dimethylamino)-phenothiazin-5-ium chloride, indigotetrasulfonic acid, indigotrisulfonic acid, 5,5'-indigodisulfonic acid sodium salt, indigomono sulfonic acid, phenosafranin, safranin T, toluylene red, and a combination thereof.

31. The method of claim 28 wherein each of the first and second pastes is packaged in a separate syringe prior to (1).

32. The method of claim 28 wherein each of the first and second pastes is packaged in a syringe of a dual-syringe assembly prior to (1), wherein each syringe in the dual-syringe assembly has an opening and a static mixer is attached to the openings and (1) is performed by dispensing the first and second pastes from the syringes through the openings and into the mixer and homogeneously mixing in the mixer to form the mixed composition, and (2) is performed in part by dispensing the mixed composition from an exit opening of the mixer.

* * * * *